(12) United States Patent
Xu

(10) Patent No.: US 9,097,657 B2
(45) Date of Patent: *Aug. 4, 2015

(54) LEAK DETECTION OF STATOR LIQUID COOLING SYSTEM

(71) Applicant: General Electric Company, Schenectady, NY (US)

(72) Inventor: James Jun Xu, Niskayuna, NY (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 98 days.

This patent is subject to a terminal disclaimer.

(21) Appl. No.: 13/948,400

(22) Filed: Jul. 23, 2013

(65) Prior Publication Data
US 2015/0028208 A1    Jan. 29, 2015

(51) Int. Cl.
*G01N 21/3504* (2014.01)
*G01M 3/22* (2006.01)
*H04N 5/33* (2006.01)

(52) U.S. Cl.
CPC ........... *G01N 21/3504* (2013.01); *G01M 3/223* (2013.01); *H04N 5/33* (2013.01)

(58) Field of Classification Search
CPC ...... G01N 21/3504; H04N 5/33; G01M 3/223
See application file for complete search history.

(56) References Cited

U.S. PATENT DOCUMENTS

| | | |
|---|---|---|
| 4,293,522 A | 10/1981 | Winkler |
| 4,300,066 A * | 11/1981 | Butler, III ........................ 310/53 |
| 4,368,694 A | 1/1983 | Ward et al. |
| 4,612,976 A | 9/1986 | Soucille et al. |
| 4,724,799 A | 2/1988 | Traiteur et al. |
| 4,755,473 A | 7/1988 | Nishino et al. |
| 4,789,635 A | 12/1988 | Ackland et al. |
| 4,790,327 A | 12/1988 | Despotis |
| 4,801,551 A | 1/1989 | Byers et al. |
| 4,822,336 A | 4/1989 | DiTraglia |
| 4,830,010 A | 5/1989 | Marshall |
| 4,851,088 A | 7/1989 | Chandrasekhar et al. |
| 4,879,999 A | 11/1989 | Leiman et al. |
| 4,945,918 A | 8/1990 | Abernathy |
| 4,957,220 A | 9/1990 | Du |
| 4,971,900 A | 11/1990 | Ahnell et al. |
| 4,994,117 A | 2/1991 | Fehder |
| 5,042,469 A | 8/1991 | Augustine |

(Continued)

FOREIGN PATENT DOCUMENTS

WO    WO 2010/049569 A1 *  5/2010

OTHER PUBLICATIONS

Worden et al., "Understanding, diagnosing, and repairing leaks in water-cooled generator stator windings", GE power systems, GER-3751A, Aug. 2001, 28 pages.*

(Continued)

*Primary Examiner* — David Porta
*Assistant Examiner* — Mindy Vu

(57) ABSTRACT

A safe, fast and accurate method of detecting a leak locale of a stator liquid cooling system especially in a plurality of stator windings in a liquid cooled generator is provided. The method includes the step of introducing a non-corrosive compatible gas or its air mixture having an infrared absorption spectrum into the plurality of stator windings of the liquid cooled generator and detecting leaks through the use of an infrared detection system. The infrared detection system includes an imaging component adapted to detect radiation at the infrared absorption spectrum of the non-corrosive gas or its air mixture. The imaging component is provided with a filter that filters wavelengths in a range encompassing the infrared absorption spectrum of the compatible, non-corrosive gas. The imaging component displays an image of the tracer gas leaking from stator liquid cooling system of the generator.

18 Claims, 4 Drawing Sheets

(56) References Cited

U.S. PATENT DOCUMENTS

| | | |
|---|---|---|
| 5,132,094 A | 7/1992 | Godec et al. |
| 5,194,134 A | 3/1993 | Futata et al. |
| 5,197,464 A | 3/1993 | Babb et al. |
| 5,200,089 A | 4/1993 | Siefert et al. |
| 5,203,320 A | 4/1993 | Augustine |
| 5,235,846 A | 8/1993 | Fanciullo |
| 5,272,087 A | 12/1993 | El Murr et al. |
| 5,291,879 A | 3/1994 | Babb et al. |
| 5,293,875 A | 3/1994 | Stone |
| 5,320,967 A | 6/1994 | Avallone et al. |
| 5,326,531 A | 7/1994 | Hahn et al. |
| 5,335,536 A | 8/1994 | Runnevik |
| 5,350,011 A | 9/1994 | Sylvester |
| 5,357,971 A | 10/1994 | Sheehan et al. |
| 5,399,535 A | 3/1995 | Whitman |
| 5,404,885 A | 4/1995 | Sheehan et al. |
| 5,432,061 A | 7/1995 | Berndt et al. |
| 5,443,991 A | 8/1995 | Godec et al. |
| 5,445,160 A | 8/1995 | Culver et al. |
| 5,558,082 A | 9/1996 | Spencer |
| 5,563,578 A | 10/1996 | Isenstein |
| 5,565,619 A | 10/1996 | Thungstrom et al. |
| 5,663,489 A | 9/1997 | Thungstrom et al. |
| 5,749,358 A | 5/1998 | Good et al. |
| 5,750,073 A | 5/1998 | Godec et al. |
| 5,798,271 A | 8/1998 | Godec et al. |
| 5,803,898 A | 9/1998 | Bashour |
| 5,820,823 A | 10/1998 | Godec et al. |
| 5,823,787 A | 10/1998 | Gonzalez et al. |
| 5,846,836 A | 12/1998 | Mallow |
| 5,857,460 A | 1/1999 | Popitz |
| 5,859,503 A | 1/1999 | Potratz |
| 5,867,105 A | 2/1999 | Hajel |
| 5,902,751 A | 5/1999 | Godec et al. |
| 5,924,995 A | 7/1999 | Klein et al. |
| 5,932,791 A | 8/1999 | Hambitzer et al. |
| 5,993,624 A | 11/1999 | Matsubara et al. |
| 6,001,064 A | 12/1999 | Weckstrom |
| 6,058,933 A | 5/2000 | Good et al. |
| 6,130,614 A | 10/2000 | Miller et al. |
| 6,159,147 A | 12/2000 | Lichter et al. |
| 6,164,277 A | 12/2000 | Merideth |
| 6,183,695 B1 | 2/2001 | Godec et al. |
| 6,190,327 B1 | 2/2001 | Isaacson et al. |
| 6,228,325 B1 | 5/2001 | Godec et al. |
| 6,247,470 B1 | 6/2001 | Ketchedjian |
| 6,250,133 B1 | 6/2001 | Schell |
| 6,318,296 B1 | 11/2001 | Nguyen |
| 6,325,978 B1 | 12/2001 | Labuda et al. |
| 6,365,022 B1 | 4/2002 | Hitchman et al. |
| 6,378,517 B1 | 4/2002 | Steen |
| 6,432,042 B1 | 8/2002 | Bashour |
| 6,496,106 B1 | 12/2002 | Rodriguez |
| 6,540,690 B1 | 4/2003 | Kanstad |
| 6,544,190 B1 | 4/2003 | Smits et al. |
| 6,584,974 B1 | 7/2003 | Ratner |
| 6,586,173 B2 | 7/2003 | Tang |
| 6,677,159 B1 | 1/2004 | Mallow |
| 6,712,762 B1 | 3/2004 | Lichter et al. |
| 6,723,285 B2 | 4/2004 | Chen et al. |
| 6,736,199 B2 | 5/2004 | Wanni et al. |
| 6,775,001 B2 | 8/2004 | Friberg et al. |
| 6,780,646 B1 | 8/2004 | Brinton |
| 6,786,182 B2 | 9/2004 | Morgandi et al. |
| 6,874,502 B1 | 4/2005 | Nashed |
| 6,923,939 B1 | 8/2005 | Nayar et al. |
| 6,969,562 B2 | 11/2005 | Su et al. |
| 6,990,980 B2 | 1/2006 | Richey, II |
| 7,017,578 B2 | 3/2006 | Tresnak et al. |
| 7,040,319 B1 | 5/2006 | Kelly et al. |
| 7,098,012 B1 | 8/2006 | Szyf et al. |
| 7,140,370 B2 | 11/2006 | Tresnak et al. |
| 7,142,105 B2 | 11/2006 | Chen |
| 7,152,598 B2 | 12/2006 | Morris et al. |
| 7,178,519 B2 | 2/2007 | Melker et al. |
| 7,199,706 B2 | 4/2007 | Dawson et al. |
| 7,229,832 B2 | 6/2007 | Nayar et al. |
| 7,235,054 B2 | 6/2007 | Eckerbom |
| 7,324,921 B2 | 1/2008 | Sugahara et al. |
| 7,326,931 B2 | 2/2008 | Frodl et al. |
| 7,335,164 B2 | 2/2008 | Mace et al. |
| 7,344,503 B2 | 3/2008 | Friedman |
| 7,353,691 B2 | 4/2008 | Salem et al. |
| 7,361,946 B2 | 4/2008 | Johnson et al. |
| 7,364,553 B2 | 4/2008 | Paz et al. |
| 7,420,473 B2 | 9/2008 | Eicken et al. |
| 7,445,602 B2 | 11/2008 | Yamamori et al. |
| 7,455,644 B2 | 11/2008 | Yamamori et al. |
| 7,464,040 B2 | 12/2008 | Joao |
| 7,465,377 B2 | 12/2008 | Paris et al. |
| 7,473,229 B2 | 1/2009 | Webber |
| 7,490,048 B2 | 2/2009 | Joao |
| 7,497,245 B2 | 3/2009 | Lorentz et al. |
| 7,564,362 B2 | 7/2009 | Cole et al. |
| 7,608,460 B2 | 10/2009 | Reed et al. |
| 7,621,270 B2 | 11/2009 | Morris et al. |
| 7,626,168 B2 | 12/2009 | Fischer et al. |
| 7,666,377 B2 | 2/2010 | Wu et al. |
| 7,675,655 B2 | 3/2010 | Marshall et al. |
| 7,712,517 B2 | 5/2010 | Gandolfi et al. |
| 7,723,711 B2 | 5/2010 | Schoo et al. |
| 7,749,169 B2 | 7/2010 | Bayer et al. |
| 7,805,256 B2 | 9/2010 | Frodl |
| 7,811,276 B2 | 10/2010 | O'Neil et al. |
| 7,811,433 B2 | 10/2010 | Manoukian et al. |
| 7,833,480 B2 | 11/2010 | Blazewics et al. |
| 7,839,290 B2 | 11/2010 | Chidakel et al. |
| 7,842,925 B2 | 11/2010 | Straub et al. |
| 7,897,109 B2 | 3/2011 | Labuda et al. |
| 7,913,541 B2 | 3/2011 | Serban et al. |
| 7,932,496 B2 | 4/2011 | Kato et al. |
| 7,967,759 B2 | 6/2011 | Couvillon, Jr. |
| 7,968,346 B2 | 6/2011 | Reed et al. |
| 7,972,824 B2 | 7/2011 | Simpson et al. |
| 7,992,561 B2 | 8/2011 | Baker, Jr. et al. |
| 7,993,586 B2 | 8/2011 | Fujiyama et al. |
| 7,997,408 B2 | 8/2011 | Peck |
| 8,028,701 B2 | 10/2011 | Al-Ali et al. |
| 8,062,221 B2 | 11/2011 | Debreczeny |
| 8,066,004 B2 | 11/2011 | Morris et al. |
| 8,083,684 B2 | 12/2011 | Palatnik |
| 8,109,272 B2 | 2/2012 | Baker, Jr. et al. |
| 8,124,419 B2 | 2/2012 | Brahim et al. |
| 8,128,574 B2 | 3/2012 | Baker, Jr. et al. |
| 8,148,167 B2 | 4/2012 | Reed et al. |
| 8,166,967 B2 | 5/2012 | Qiu |
| 8,183,052 B2 | 5/2012 | Reed et al. |
| 8,188,485 B2 | 5/2012 | Schoo et al. |
| 8,230,720 B2 | 7/2012 | Serban et al. |
| 8,233,954 B2 | 7/2012 | Kling et al. |
| 8,236,459 B2 | 8/2012 | Ha et al. |
| 8,256,414 B2 | 9/2012 | Ratner |
| 8,261,742 B2 | 9/2012 | Strothmann et al. |
| 8,274,393 B2 | 9/2012 | Ales et al. |
| 8,283,918 B2 | 10/2012 | Park et al. |
| 8,334,975 B1 | 12/2012 | Cook |
| 8,335,992 B2 | 12/2012 | Skidmore et al. |
| 2008/0110243 A1* | 5/2008 | Burke et al. ............ 73/38 |
| 2008/0231719 A1* | 9/2008 | Benson et al. ............ 348/222.1 |
| 2012/0330224 A1* | 12/2012 | Mailova et al. ............ 604/24 |

OTHER PUBLICATIONS

English translation obtained from WIPO of WO 2010/049569, May 6, 2010, 27 pages.*

U.S. Appl. No. 13/911,567, filed Jun. 6, 2013, James Jun Xu.

Xu, J. and A Garton, "The Chemical Composition of Water Trees in EPR Cable Insulation, IEEE Transactions, Dielectrics and Electrical Insulation", Feb. 1994, 1, 18-24.

* cited by examiner

LEAK DETECTION OF STATOR LIQUID COOLING SYSTEM

TECHNICAL FIELD

The subject matter disclosed herein generally relates to detection of leaks and more particularly to the detection of coolant leaks into a stator liquid cooling system in turbine generators.

BACKGROUND

Large turbine generators are typically cooled with a light density gas. Hydrogen ($H_2$) has been widely used as a coolant due to its desirable thermophysical properties including low windage friction, high heat dissipation capability and high resistance to corona discharge when compared to other cooling gas options. Additionally, $H_2$ has the advantage of being readily accessible and inexpensive.

Among $H_2$ cooled generators there is a type of liquid cooled generators whose inner spaces are cooled with $H_2$ while the stator windings are cooled with a liquid coolant. The stator windings typically include a plurality of hollow copper strands which serve as conduits for the liquid coolant. A typical stator winding includes at least one stator bar coupled to a bar clip and a header coupled to a source of liquid coolant which is conveyed by a pipe through a hydraulic connection to the bar clip. Liquid coolant flows from an inlet coolant header into the flow passages formed by the plethora of hollow copper strands within the stator bar and then flows outwardly into an outlet coolant header for flow into a reservoir. The liquid coolant, such as water, is supplied to the windings via a closed loop system including a heat exchanger and a deionizer.

Liquid cooled generators offer high efficiency, exceptional reliability, quick and simple installation and minimal maintenance costs. However, during operation, the liquid cooled stator windings are subject to an environment of thermal shocks, cyclic duty, corrosion, mechanical vibrations, and electromagnetic stresses which may give rise to the potential for leaks. Leaks in liquid cooled stator windings may originate at any of a number of components, such as copper tubing, pipes, piping connections, among others.

U.S. Pat. No. 7,353,691 teaches a turbine generator leak detection method involving a flow monitoring system that detects $H_2$ leaking into a water cooling system. A variety of methods of leak detection have been used when the leakage is higher than recommended. Among conventional leak test methods, one method involves sniffing detection of $H_2$ in the water tank vent of the SLCS. If a leak is detected, a balloon (bag) test may be conducted to determine the leakage rate. However, the leak locale is difficult to determine during the operation, or during outage service using this approach.

Another method of detecting leaks is to perform pressure decay, and vacuum decay tests to confirm that the stator winding is capable of holding pressure and vacuum. If the pressure within the stator winding falls too rapidly after the stator winding has been pressurized with compressed air, or if the pressure rises too rapidly after air has been evacuated, then a leak that requires further attention is indicated.

If a leak is indicated by pressure and/or vacuum decay testing; then helium tracer gas testing may be used. Helium tracer gas may be performed around all joints such as connection ring to pipes, clip to stator braze joint, water or hydrogen cooled high voltage bushings and a long list of places of interest. Helium tracer gas testing has the disadvantage that it is time-consuming for inspecting the entire winding and requires access to the whole winding. To detect small leaks, the sniffer detector must be brought within 2 to 3 inches of the leak. Because it is nearly impossible to cover every square inch of the winding, tracer test techniques are used to test only the most probable leak sites. Such testing cannot provide confidence that the entire winding is leak-tight.

Conventional leak detection methods are time consuming and, in some cases, may miss some of the leaks. A stator winding that passes a conventional leak test is not guaranteed to be leak free. Additionally, each cycle of the testing requires monitoring for at least 24 hours, if not days, as more than hundreds of those connection and joints may be leak locales. Additionally, conventional methods of leak detection require the detector to be in close proximity to the source of the leak and rely on educated or experienced guesses. This takes considerable time to implement. These methods do not provide a remote, sensitive, accurate, fast detection capability.

BRIEF DESCRIPTION OF THE INVENTION

The disclosure provides methods and systems and apparatus for the remote, sensitive, accurate, safe, and fast detection of leak locales from a stator winding of an SLCS of a liquid cooled turbine generator. The methods disclosed are safe from a health, environmental and safety point of view and avoid corrosion of generator components.

In accordance with one exemplary non-limiting embodiment, the invention relates to a method and apparatus for detecting a leak locale in an SLCS of a liquid cooled generator. The apparatus includes a subsystem for introducing a pressurized non-corrosive gas having an infrared absorption spectrum into a plurality of stator windings of the SLCS of the liquid cooled generator. The apparatus further includes an imaging component adapted to detect radiation at the infrared absorption spectrum of the pressurized non-corrosive gas and has a filter that filters wavelengths in a range encompassing the infrared absorption spectrum of the non-corrosive gas. The imaging device may be distally disposed in the vicinity of the plurality of stator windings.

In another embodiment, the SLCS is drained, and the stator windings of the SLCS are purged with dry air. $CO_2$ is then introduced into the stator winding of the SLCS and pressurized up to more than 15 psig, more preferably up to 30 psig or 45 psig.

In another embodiment, a system for detecting a gas leak locale in a stator winding of an SLCS of a liquid cooled generator is provided. The system includes a source of tracer gas and a subsystem for introducing the tracer gas into the stator windings of the SLCS. The system further includes an infrared imaging device adapted to display an image of the tracer gas. The system may include a source of a mixture of gas with dry air.

In another embodiment, a method for detecting a leak locale of a liquid coolant from an SLCS in a generator is provided. The method includes disposing an infrared imaging system having a cold detector response of between 3 µm to 5 µm with a field of view encompassing at least a portion of the generator. The method includes disconnecting a plurality of stator windings from the SLCS. Thereafter a tracer gas is introduced into the stator windings, the tracer gas having an absorption spectrum of between 3 µm and 5 µm. The method includes filtering the radiation received by the infrared imaging system in the absorption spectrum of the tracer gas, and displaying an image of tracer gas leaking from the stator windings.

BRIEF DESCRIPTION OF THE DRAWINGS

Other features and advantages of the present invention will be apparent from the following more detailed description of the preferred embodiment, taken in conjunction with the accompanying drawings which illustrate, by way of example, the principles of certain aspects of the invention.

DETAILED DESCRIPTION OF THE INVENTION

Aspects of the present disclosure include a system for detecting leaks in an SLCS of a liquid cooled turbine generator through the introduction of an environmentally safe non-corrosive tracer gas into the stator windings that are disconnected from the SLCS during the detection test. An infrared imaging device adapted to display an image of the escaping tracer gas is provided. The utility of the present disclosure is amplified when used to detect leaks in the stator windings of the SLCS where hundreds of joints may be the sources of potential leaks.

Figure 1:
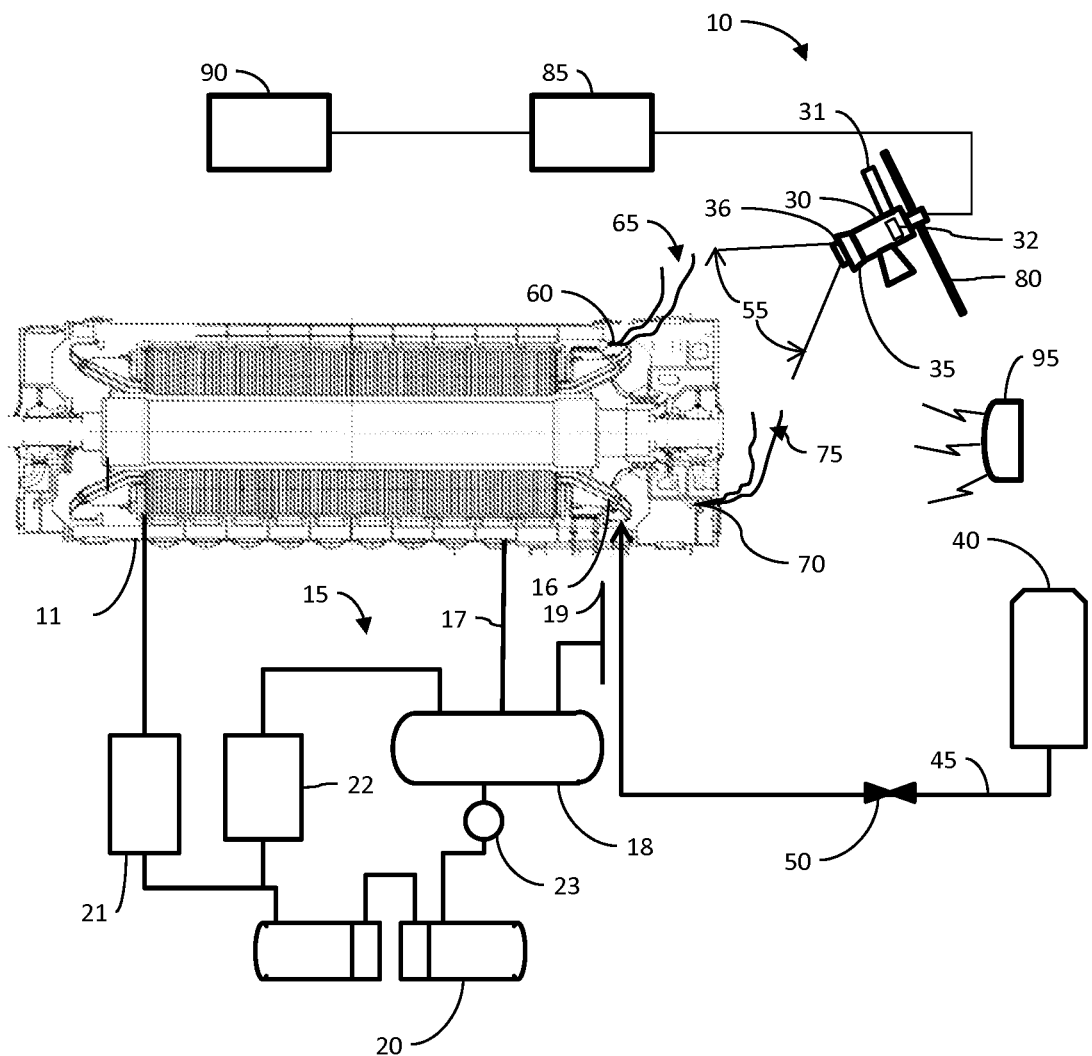
FIG. 1 is a schematic of a leak detection system for detecting leaks in an SLCS.
Figure 2:
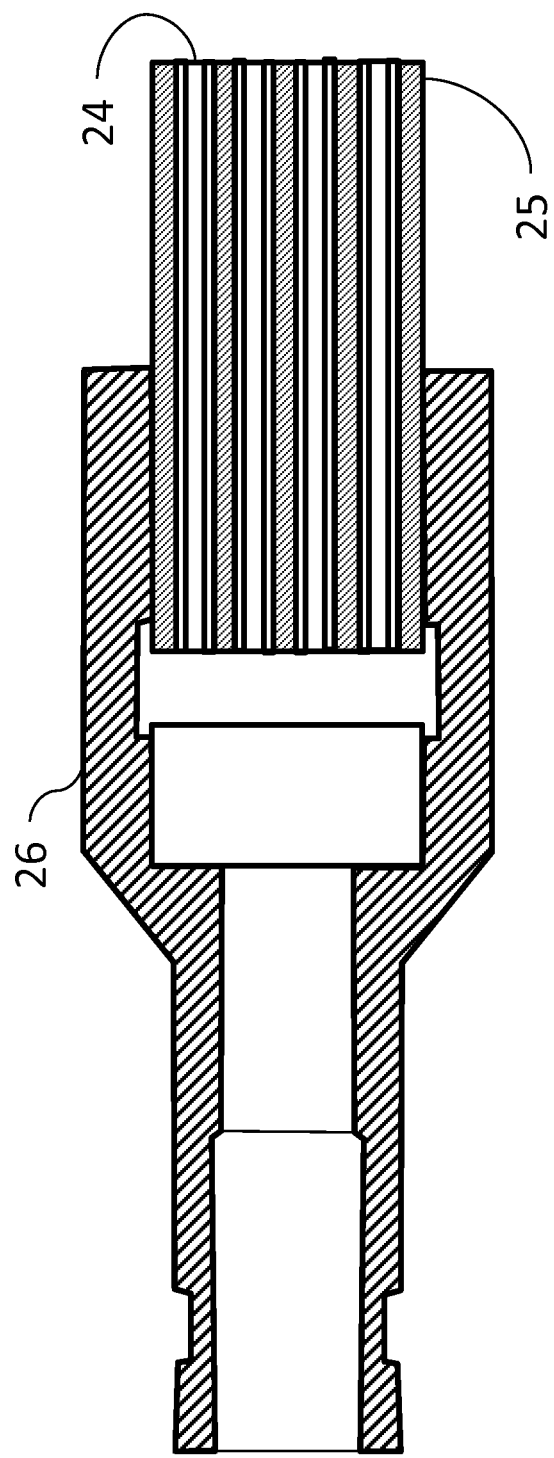
FIG. 2 is a cross section schematic of a portion of a stator winding.

Illustrated in FIG. 1 is a schematic of a leak detection system 10 for use in detecting leaks in a liquid cooled turbine generator 11. The liquid cooled turbine generator 11 includes an SLCS 15 having a plurality of stator windings 16 disposed in the liquid cooled turbine generator 11. The SLCS 15 also includes conduit 17 coupled to the stator windings 16 and a liquid coolant reservoir 18. The liquid coolant reservoir 18 may be vented to the atmosphere through vent 19. The liquid coolant reservoir 18 is coupled to heat exchangers 20, which are in turn coupled to the stator windings 16 through an assembly of filters and strainers generally identified as assembly 21. A deionizer 22 may also be provided. In operation, liquid coolant is pumped by pump 23 from the liquid coolant reservoir 18 through the heat exchangers 20 and into the stator windings 16. As shown in FIG. 2, the stator windings 16 may include a plurality of hollow copper strands 24, and a plurality of solid copper conductors 25 that are coupled to a header 26. The liquid coolant flows through the hollow copper strands 24 effectively cooling the stator windings 16.

Referring again to FIG. 1, the leak detection system 10 includes an infrared imaging device 30, which may contain an image screen 31 and a detection device 32. The infrared imaging device 30 may be a handheld mid wave infrared camera or a portable or mobile imaging device. The infrared imaging device 30 may be adapted to provide a cold detector response of 3 µm to 5 µm and may be further spectrally adapted to provide a detector response of approximately 3.9 µm to 4.6 µm through the use of a filter 35. This makes the infrared imaging device 30 more responsive to a tracer gas cloud from the potential leak locations.

In one embodiment, detection of a leak locale of the SLCS 15 may start with the section of the SLCS 15 that houses the stator windings 16 which extend outside of the liquid cooled turbine generator 11. In this embodiment, the leak detection system 10 includes a source 40 of tracer gas that is coupled to the interior of the stator windings 16 of the SLCS 15. Tracer gas flows through a conduit 45 having a control valve 50 that controls the amount and pressure of tracer gas introduced into the stator windings 16 of the SLCS 15. The tracer gas is preferably cooled or heated several degrees Celsius, and is environmentally friendly and non-corrosive. The tracer gas may be introduced into the stator windings 16 at a rate of about 24 liters per second, which corresponds to a rate of 4.7 liters/second per tracer gas cylinder. The tracer gas may fill the internal volume of the stator windings 16. The tracer gas should be environmentally safe from the point of view of toxicity and have the least greenhouse effect. Additionally, the tracer gas should not cause corrosive damage to the inner walls of pipes or the hollowed copper strands of stator windings 16. The tracer gas should also have an appropriate density ranging from 0.5 to 2.5 g/liter.

The infrared imaging device 30, which may include the image screen 31 and the detection device 32, is adapted to visualize the absorptive and emissive properties of tracer gases allowing the user the ability to discern the tracer gas from its host environment. The filter 35 is designed to transmit in an IR spectral region that is coincident in wavelength with vibrational/rotational energy transitions of the molecular bonds of the tracer gas. These transitions are typically strongly coupled to the field via dipole moment changes in the molecule and are common to many types of gases and vapors. The detector of the infrared imaging device 30 may be cooled to 77° K. or approximately −196° C. in an Integrated Cooler Detector Assembly (or Integrated Dewar Cooler Assembly, IDCA), to increase the sensitivity of remote imaging of tracer gases. The thermal sensitivity is typically less than 20 mK, and preferably less than 14 mK. The filter 35 may be mounted on an imaging lens 36, or behind the imaging lens 36, or inside the IDCA assembly for increased versatility or increased sensitivity. The filter 35 has a mid-wavelength of 3.9 to 4.6 microns, or more preferably 4.1 µm to 4.5 µm. The infrared imaging device 30 may be calibrated with temperature and tuned with the largest image contrast possible using modes of absorption, reflection or scattering so that the exact pressure, flow rate and temperature gradient of leaking tracer gas can be identified from varying detection distances. The infrared imaging device 30 may be portable and capable of scanning large sections of stator windings 16 of the SLCS 15. After completion of leak detection in the stator windings 16, the external portion of the SLCS 15 may be examined for additional leak locations. If the infrared imaging device 30 is directed at the stator windings 16 without a tracer gas leak, then objects in the field of view will emit and reflect infrared radiation through the filter 35 of the infrared imaging device 30, and no discernible tracer gas cloud would be displayed. If there is a leak within the field of view 55 of the infrared imaging device 30 such as at leak point 60, a leak gas cloud 65 will be generated between the SLCS 15 and the infrared imaging device 30. The leak gas cloud 65 will absorb radiation in the band pass range of the filter 35, and consequently the amount of radiation passing through the leak gas cloud 65 and returning to the cold detector will be reduced, thereby making the leak gas cloud 65 visible through image screen 31 of the infrared imaging device 30. If there is a leak outside of the field of view 55 of the infrared imaging device 30, such as at leak point 70, portions of a leak gas cloud 75 would still be detected by moving the infrared imaging device 30.

The infrared imaging device 30 may also be mounted on a support 80. The infrared imaging device 30 may be coupled to an image analyzer 85, which in turn may be coupled to a control system 90. The infrared imaging device 30 may be moved periodically or continuously, to automatically detect leaks during the outage period. The infrared imaging device 30, the image analyzer 85 and the control system 90 may be separate components or an integrated assembly.

The infrared imaging device 30 may have a mountable 25 mm (~1 inch) imaging lens 36 to enable focusing of stator windings 16 of the SLCS 15 of the liquid cooled turbine generator 11 from a distance of 3 feet to 50 feet. Distances of greater than 50 feet may require mounting an imaging lens 36 of 2 inches or more. The resulting field of view 55 may allow the detection of hundreds of potential leak locales at the braze joints and pipe joints of the SLCS 15 in a single view. A preferred mode of practice also includes positioning the imaging lens 36 perpendicular to the direction of potential tracer gas cloud, that is, parallel to the direction of pipeline length direction. The other preferred mode of practice includes the placement of a heated ultra-thin sheet whose temperature is 5-20° C./° F. higher than that of atmosphere surrounding the suspicious leak locales. This allows for a rigorous and versatile observation of leaks. One may focus to observe the cloud leaking out. One may also observe the color change on the heated sheet to indirectly indicate that a cooler tracer gas is leaking near the area of the color change on the sheet. Yet another mode of practice is to introduce $CO_2$ that is 5-20° C./° F. cooler than that of atmosphere into the stator windings 16.

Figure 3:
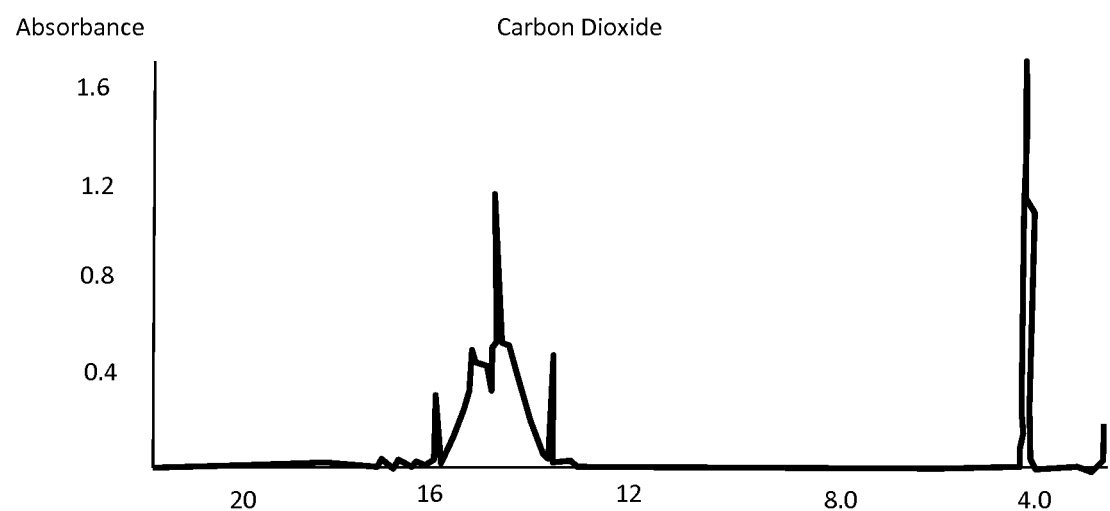
FIG. 3 is a chart showing the main mid and long wavelength absorption regions of the absorption spectrum of $CO_2$.

For many gases, the capability to absorb infrared radiation and to emit photons depends on the wavelength of the radiation. In other words, their degree of transparency varies with wavelength. There may be infrared wavelengths where they are essentially opaque due to absorption. Gases having the appropriate IR absorption spectrum include hydrocarbons. Preferably the tracer gas may be $CO_2$, a natural cold gas stored in pressurized cylinders in liquid form around −80° C. Illustrated in FIG. 3 is the absorption spectrum of $CO_2$. As can be seen from the charts, $CO_2$ has a maximal absorption peak near 4 µm.

In one embodiment, the infrared imaging device 30 may be a thermographic infrared camera adapted to detect radiation in the infrared range of the electromagnetic spectrum (between 13 µm and 16 µm). Because the amount of radiation emitted by an object increases with temperature, infrared imaging device 30 may be used to display variations in temperature. When viewed through a thermographic infrared camera, warm or cold objects stand out well against cooler/warmer backgrounds. The infrared imaging device 30 may be used to detect gas temperature that is at least 0.1° C. or ° F. higher or lower, and preferably 1° C. or ° F. higher or lower, or even more preferably, 5-20° C. or ° F. higher or lower than that of atmosphere surrounding the stator windings 16. The infrared imaging device 30 may be used in a passive thermography system where the plume of leaking tracer gas is at a higher or lower temperature than the background. Alternately, the infrared imaging device 30 may be used as part of an active thermography system that utilizes an energy source to produce a thermal contrast between the plume of leaking tracer gas and the background. In the latter case, an infrared heating light 95 may be used to heat the local atmosphere of suspicious leak locales in order to create contrast with a leak gas cloud 65 escaping from a leak point 60. The distance, response time, angle of detection and image resolution may vary the requirement for the preferred temperature gradient of the tracer gas.

Figure 4:
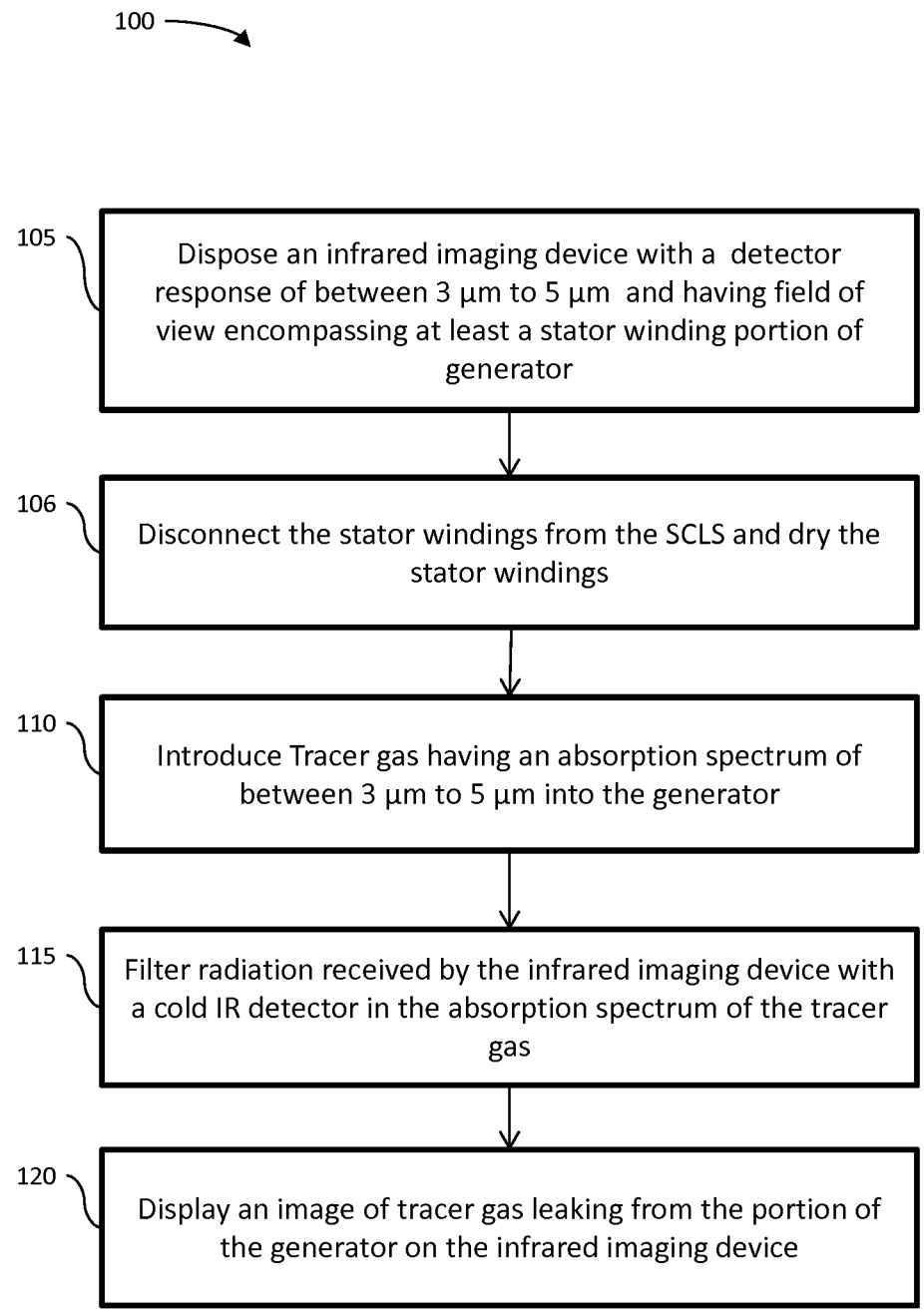
FIG. 4 is a flow chart of a method for detecting a leak locale of an SLCS in a liquid cooled turbine generator.

FIG. 4 is a flow chart of a method 100 for detecting a leak of a liquid coolant in an SLCS 15 of a liquid cooled turbine generator 11.

In step 105, an infrared imaging device 30 is disposed with a field of view encompassing at least one of a plurality of stator windings 16 of the liquid cooled turbine generator 11.

In step 106, the SLCS 15 is disconnected from the stator windings 16 and the stator windings 16 are dried with air.

In step 110, a tracer gas is introduced into the SLCS 15. The tracer gas will preferably have an absorption spectrum between 3 µm to 5 µm and more preferably between 3.8 µm to 4.6 µm. The tracer gas may be introduced from the stator windings 16 of the liquid cooled turbine generator 11. The tracer gas may have a density of between 0.5 to 2.5 g/liter. The tracer gas may be $CO_2$ and may be introduced into stator windings 16 until the $CO_2$ fills the inner volume of the stator windings 16. The tracer gas may be pressurized in the stator windings 16 up to 45 psig when there is a need to identify the smallest leak locales.

In step 115, the radiation received by the infrared imaging device 30 is filtered in the absorption spectrum of the tracer gas with a cold IR detector.

In step 120, an image of the tracer gas leaking from the stator windings 16 of the liquid cooled turbine generator 11 is displayed on the infrared imaging device 30.

In yet another embodiment, a safe, non-corrosive, distantly detectable gas other than $CO_2$ may be provided. The gas acts as a gas sensor and fills into the SLCS 15 of the liquid cooled turbine generator 11 during its outage service. The method of gradually purging the inert tracer gas is compatible with generator safe operation protocol.

In yet another embodiment, the air may be cooled or heated prior to entering the SLCS 15. Air temperature of 3° C., or more preferably 5° C. to 20° C. above the ambient of any season may be preferred.

The embodiments set forth above do not exclude the use of a combination of leak detection methods. For instance, the detection may start with a conventional method, such as air pressure decay of the stator winding after draining the liquid coolant from the pipe lines. Then a vacuum decay test may be performed, followed by a helium probe sniffing around the most probable leak locales while the stator winding is connected to a mass spectrometer. After the preliminary vacuum and helium test, which may be time-consuming, the vacuumed stator winding is introduced with CO2 for the infrared imaging detection.

Where the definition of terms departs from the commonly used meaning of the term, applicant intends to utilize the definitions provided below, unless specifically indicated.

The terminology used herein is for the purpose of describing particular embodiments only and is not intended to be limiting of the invention. Where the definition of terms departs from the commonly used meaning of the term, applicant intends to utilize the definitions provided herein, unless specifically indicated. The singular forms "a", "an" and "the" are intended to include the plural forms as well, unless the context clearly indicates otherwise. It will be understood that, although the terms first, second, etc. may be used to describe various elements, these elements should not be limited by these terms. These terms are only used to distinguish one element from another. The term "and/or" includes any, and all, combinations of one or more of the associated listed items. The phrases "coupled to" and "coupled with" contemplates direct or indirect coupling.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements.

What is claimed:

1. An apparatus for detecting a leak locale in stator liquid cooling system of a liquid cooled generator, the apparatus comprising:

a subsystem for introducing a pressurized non-corrosive gas having an infrared absorption spectrum into a plurality of stator windings of the stator liquid cooling system; and an imaging component adapted to detect radiation at the infrared absorption spectrum of the pressurized non-corrosive gas, the imaging component having a filter that filters wavelengths in a range encompassing the infrared absorption spectrum of the pressurized non-corrosive gas, wherein the subsystem for introducing the pressurized non-corrosive gas comprises means for draining liquid coolant from the plurality of stator windings; means for drying the plurality of stator windings with air; and means for introducing a mixture of air and carbon dioxide at a predetermined temperature, wherein the mixture of air and carbon dioxide has a content ratio of carbon dioxide of between 0.1% to 100%.

2. The apparatus of claim 1, wherein the imaging component comprises an infrared imaging device with a cooled detector having a spectral response between 3 µm and 5 µm.

3. The apparatus of claim 2, wherein the filter narrows a detector response of the infrared imaging device to between 3.8 µm and 4.6 µm.

4. The apparatus of claim 1, wherein the pressurized non-corrosive gas has an absorption spectrum of between 3.8 µm and 4.6 µm.

5. The apparatus of claim 1, wherein the pressurized non-corrosive gas contains a gas selected from among a group comprising hydrocarbons, and carbon dioxide.

6. The apparatus of claim 1, wherein the imaging component comprises a thermographic infrared camera.

7. The apparatus of claim 1, wherein the subsystem for introducing a pressurized non-corrosive gas comprises:
a source of the pressurized non-corrosive gas; and
a control valve.

8. A system for detecting a gas leak locale of a stator liquid cooling system in a liquid cooled generator, the system comprising:
a source of tracer gas;
a subsystem for introducing tracer gas into a plurality of stator winding after it is disconnected from the stator liquid cooling system; and
an infrared imaging device adapted to display an image of the tracer gas from a distance, wherein the subsystem for introducing the tracer gas comprises means for draining liquid coolant from the plurality of stator windings; means for drying the plurality of stator windings with air; and means for introducing a mixture of air and carbon dioxide at a predetermined temperature, wherein the mixture of air and carbon dioxide has a content ratio of carbon dioxide of between 0.1% to 100%.

9. The system of claim 8, wherein the tracer gas is a non-corrosive gas.

10. The system of claim 8, wherein the tracer gas is carbon dioxide.

11. The system of claim 8, wherein the infrared imaging device is a passive infrared imaging system.

12. The system of claim 8, wherein the infrared imaging device is a manually operated active infrared imaging system.

13. The system of claim 8, wherein the tracer gas is a mixture of carbon dioxide and air.

14. The system of claim 8, wherein the infrared imaging device comprises a filter and a lens.

15. A method for detecting a leak locale of a liquid coolant from a stator liquid cooling system in a generator, the method comprising:
disposing an infrared imaging system having a detector response of between 3 µm to 5 µm with a field of view encompassing at least a portion of the generator;
disconnecting a plurality of stator windings from the stator liquid cooling system;
introducing a tracer gas into the plurality of stator windings, the tracer gas having an absorption spectrum of between 3 µm and 5 µm;
filtering radiation received by the infrared imaging system in the absorption spectrum of the tracer gas; and
displaying an image of tracer gas leaking from the plurality of stator windings on an infrared imaging system at a distance, wherein the step of introducing the tracer gas comprises:
draining liquid coolant from the plurality of stator windings;
drying the plurality of stator windings with air; and
introducing a mixture of air and carbon dioxide at a predetermined temperature, wherein the mixture of air and carbon dioxide has a content ratio of carbon dioxide of between 0.1% to 100%.

16. The method of claim 15, wherein the tracer gas has a density of between 0.5 to 2.5 igniter.

17. The method of claim 15, wherein the tracer gas has an absorption spectrum of between 3.8 µm to 4.6 µm.

18. The method of claim 15, wherein the step of introducing the tracer gas comprises introducing carbon dioxide until the carbon dioxide fills the plurality of stator windings.

* * * * *

UNITED STATES PATENT AND TRADEMARK OFFICE
CERTIFICATE OF CORRECTION

PATENT NO. : 9,097,657 B2
APPLICATION NO. : 13/948400
DATED : August 4, 2015
INVENTOR(S) : Xu Page 1 of 1

It is certified that error appears in the above-identified patent and that said Letters Patent is hereby corrected as shown below:

In the Claims

In Column 8, Line 41, in Claim 16, delete "igniter." and insert -- g/liter. --, therefor.

Signed and Sealed this
Twenty-first Day of June, 2016

Michelle K. Lee
*Director of the United States Patent and Trademark Office*